United States Patent
Yamaguchi (10) Patent No.: US 7,742,570 B2
(45) Date of Patent: Jun. 22, 2010

(54) X-RAY RADIOGRAPHIC APPARATUS AND METHOD

(75) Inventor: Yoshitaka Yamaguchi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 12/414,369

(22) Filed: Mar. 30, 2009

(65) Prior Publication Data

US 2009/0245464 A1 Oct. 1, 2009

(30) Foreign Application Priority Data

Mar. 31, 2008 (JP) .............................. 2008-093533

(51) Int. Cl.
*H05G 1/60* (2006.01)

(52) U.S. Cl. ..................................... 378/98.12; 378/62

(58) Field of Classification Search .............. 378/98.12, 378/163, 175, 172, 177, 181, 197, 62

See application file for complete search history.

(56) References Cited

U.S. PATENT DOCUMENTS 6,473,489 B2 * 10/2002 Bani-Hashemi et al. ....... 378/63
6,895,076 B2    5/2005 Halsmer et al.
7,142,632 B2 * 11/2006 Atzinger et al. ............... 378/62
2005/0169427 A1 * 8/2005 Halsmer et al. .......... 378/98.12
2008/0152088 A1 * 6/2008 Wang et al. .............. 378/98.12

FOREIGN PATENT DOCUMENTS

| EP | 1 484 016 A1 | 12/2004 |
|----|--------------|---------|
| EP | 1 484 017 A1 | 12/2004 |
| JP | 2000-232976 A | 8/2000 |
| JP | 2004-358254 A | 12/2004 |
| JP | 2006-500126 A | 1/2006 |
| WO | 2004-028368 A1 | 4/2004 |

* cited by examiner

*Primary Examiner*—Hoon Song
(74) *Attorney, Agent, or Firm*—Sughrue Mion, PLLC (57) ABSTRACT

An entire area of an FPD on which an alignment marker provided in a screen is projected is set in advance as a fixed overlapping area ($C_{top}$ to $C_{bottom}$) according to the long length imaging area and/or the X-ray source position. When determining a plurality of field-of-view area areas for dividing an imaging area for long length imaging into a plurality of areas and taking images, the field-of-view areas ($FOV_{NT}$ to $FOV_{NB}$) and the FPD positions $P_N$ corresponding to the respective field-of-view areas are determined so that adjacent field-of-view areas overlap each other at the set fixed overlapping area. The X-ray source height, the X-ray irradiation direction, the collimator aperture angle and the FPD position are controlled so as to apply an X-ray only to each of the determined field-of-view areas.

11 Claims, 12 Drawing Sheets

X-RAY RADIOGRAPHIC APPARATUS AND METHOD

BACKGROUND OF THE INVENTION

1. Field of the Invention

The present invention relates to an X-ray radiographic apparatus and method, and specifically relates to a technique for obtaining one long length of X-ray image by taking plural X-ray images and connecting these X-ray images.

2. Description of the Related Art

In plain X-ray radiography, a long length of image is sometime taken for a region with a long length, such as the entire backbone or the entire legs.

Conventional computed radiography (CR) is X-ray radiography using a storage phosphor sheet (imaging plate: IP) instead of an X-ray film. In the CR, when taking a long length of image, images are taken with IPs overlapped each other, and a long length of image is obtained by combining images read from the respective IPs (Japanese Patent Application Laid-Open No. 2000-232976). Also, in this case, more accurate alignment can be performed by providing markers made of, e.g., lead, in the region where the IPs overlap each other.

Meanwhile, in recent years, for plain X-ray radiography, DR (digital radiography) has been proposed as an improvement from the aforementioned CR method. In the DR, an X-ray is converted into electrical signals and read as they are by means of an X-ray flat panel detector (FPD) with a large area, and long-length imaging using this FPD has also been performed.

Examples of long length imaging methods mainly include: an X-ray tube turning method in which plural images are taken while an X-ray tube is turning (Japanese Patent Application Laid-Open No. 2004-358254); and an X-ray tube parallel movement method in which plural images are taken while an X-ray tube being moved in parallel to itself (Japanese National Publication of International Patent Application No. 2006-500126).

SUMMARY OF THE INVENTION

In long length imaging, an image of a part of a subject is taken at plural positions by moving the position of the FPD, and the entire image is obtained by connecting the images. It is preferable to provide a screen for supporting a subject, at a predetermined position ahead of the FPD so as to prevent the subject from moving during taking plural X-ray images.

It is also preferable that: markers, which provide marks for alignment, are provided in the screen; when taking X-ray images while moving the FPD, the X-ray images are taken so that the markers are positioned in the overlapping areas of the images; and the markers shown in the respective images are used for alignment.

Figure 12A:
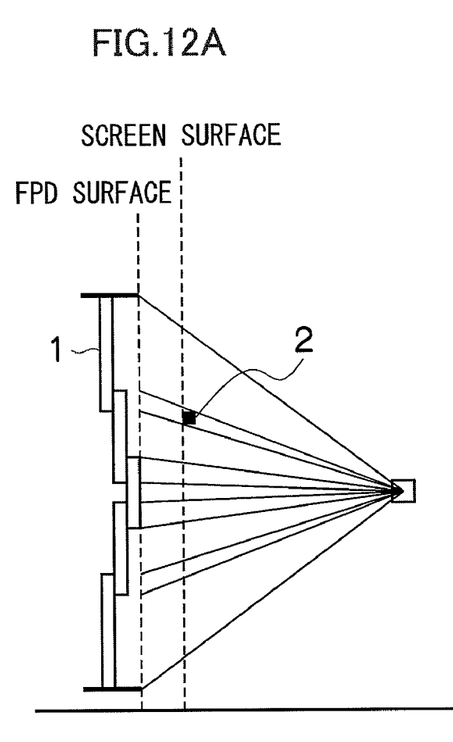
FIGS. 12A and 12B are diagrams illustrating variation of a position on which a maker is projected, depending on the position of an X-ray source.
Figure 12B:
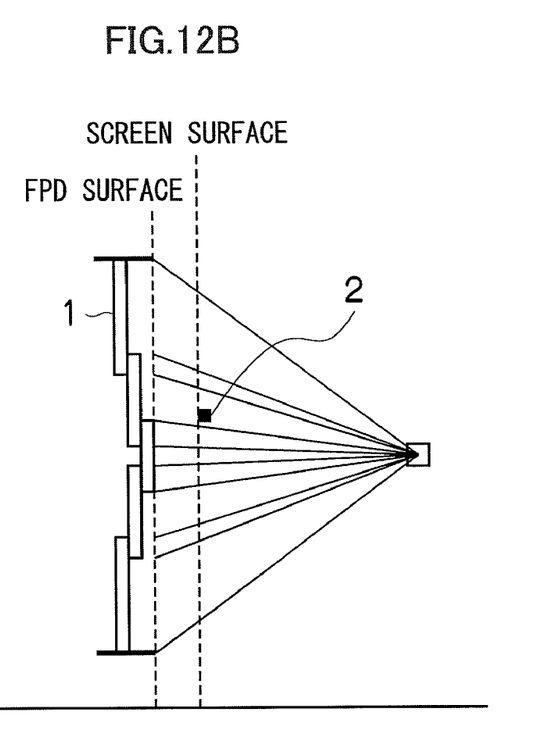

However, when markers are provided in the overlapping areas as described above, the relationship between a FPD 1 and a marker 2 varies depending on the long length imaging area as illustrated in FIGS. 12A and 12B. Also, since there is a space between the screen and the FPD, the position in which the marker 2 is shown also varies depending on the position of the X-ray source.

In order to unfailingly position a marker in an overlapping area of an FPD regardless of the long length imaging area or the position of the X-ray source, providing multiple markers in a screen so as to position any of the markers in the overlapping area can be contemplated. In this case, however, a problem may arise in the markers may be obstacles for diagnosis.

Meanwhile, when re-setting the marker each time the long-length imaging area and/or X-ray source position is set, a problem also arise because it takes a lot of trouble.

The present invention has been made in view of the aforementioned circumstances, and an object of the present invention is to provide an X-ray radiographic apparatus and method that enables easily performing long length imaging in which an alignment marker is unfailingly positioned in an overlapping area of an X-ray plat panel detector regardless of the long-length imaging area and/or the X-ray source position.

In order to achieve the above object, an X-ray radiographic apparatus according to a first aspect of the present invention comprises: an X-ray generation unit including an X-ray source, the X-ray source including an X-ray tube and an X-ray movable diaphragm that adjusts a field of view of an X-ray provided from the X-ray tube, and a lifting and lowering device that moves the X-ray source at least in a vertical direction; an X-ray imaging unit including an X-ray flat panel detector that converts an incoming X-ray into electrical signals, and an upright stand that moves the X-ray flat panel detector in the vertical direction; a screen provided at a predetermined position ahead of the X-ray imaging unit, the screen supporting a subject to prevent the subject from moving, the screen being provided with a marker for alignment between a plurality of X-ray images taken during long length imaging; a fixed overlapping area setting device that sets an area of the X-ray flat panel detector on which the marker may be projected as a fixed overlapping area, according to a moveable range of the X-ray source during long length imaging; an imaging area setting device that sets an imaging area for the long length imaging; a field-of-view area determination device that determines a plurality of field-of-view areas when dividing the set imaging area into a plurality of areas and taking images, the field-of-view area determination device determining each of the field-of-view areas so that adjacent field-of-view areas overlap each other at the determined fixed overlapping area; a position determination device that determines a position to which the X-ray flat panel detector is moved for each of the field-of-view areas determined by the field-of-view area determination device so that an X-ray is applied to the field-of-view area; an upright stand control device that controls the upright stand so that the X-ray flat panel detector is sequentially moved to one of the positions determined by the position determination device for each exposure during the long length imaging; and an X-ray control device that controls the X-ray generation unit according to one of the field-of-view areas determined by the field-of-view area determination device for each exposure during the long length imaging so that an X-ray is applied only to the field-of-view area.

In other words, since the position in which an alignment marker provided on a screen is projected on the X-ray flat panel detector varies depending on the long length imaging area and/or the X-ray source position, and the entire area of these varying positions of the marker is set to be a fixed overlapping area. Then, when determining a plurality of field-of-view areas for dividing an imaging area for long length imaging into a plurality of areas and taking images, the respective field-of-view areas are determined so that the fixed overlapping areas for adjacent field-of-view areas overlap each other, and meanwhile, the position to which the X-ray flat plane detector is moved is determined for each of the determined field-of-view areas so that an X-ray is applied to the field-of-view area. As a result of controlling the X-ray generation unit so that an X-ray is applied only to each of the field-of-view areas determined as described above and controlling the position to which the X-ray flat panel detector is moved, the marker can unfailingly be projected on an overlapping area (fixed overlapping area) of the X-ray flat panel detector regardless of the long length imaging area and/or the X-ray source position. Also, when connecting adjacent X-ray images, the images are connected so that the markers shown in the fixed overlapping areas are aligned with each other, enabling provision of a long-length image in which the images are connected with good accuracy.

A second aspect of the present invention provides the X-ray radiographic apparatus according to the first aspect, wherein the fixed overlapping area is an area from a maximum height position to a minimum height position of the X-ray flat panel detector on which the marker is projected, the area being determined based on horizontal distances among the X-ray generation unit, the screen and the X-ray imaging unit, a position at which the marker is provided, and a minimum incident angle and a maximum incident angle of an X-ray that can be applied to the marker during the long length imaging.

A third aspect of the present invention provides the X-ray radiographic apparatus according to the first or second aspect, wherein: a plurality of the markers are provided in the screen at an interval smaller than a length in the vertical direction of the X-ray flat panel detector; and the fixed overlapping area setting device sets the fixed overlapping area for each of the markers. This enables long length imaging in which three or more images are connected, and also enables taking an of any long-length region of a subject such as the entire backbone or the entire legs.

A fourth aspect of the present invention provides the X-ray radiographic apparatus according to any of the first to third aspects, wherein the position determination device determines the position to which the X-ray flat panel detector is moved so that a center position of one of the field-of-view areas and a center position of the X-ray flat panel detector correspond to each other, a top edge position of one of the field-of-view areas and a top edge position of the X-ray flat panel detector correspond to each other, or a bottom edge position of one of the field-of-view areas and a bottom edge position of the X-ray flat panel detector correspond to each other. In other words, the position of the X-ray flat panel detector relative to a determined field-of-view area is determined on any of a center basis, a top edge basis and a bottom edge basis.

A fifth aspect of the present invention provides the X-ray radiographic apparatus according to any of the first to fourth aspects, wherein the X-ray control device, upon determination of a field-of-view area by the field-of-view area determination device, sets a height position in the vertical direction of the X-ray source to be equal to a height position of a center position of the imaging area set by the imaging area setting device, and controls an X-ray irradiation direction of an X-ray from the X-ray source and an aperture angle provided by the X-ray movable diaphragm so that the X-ray is applied only to the determined field-of-view area, based on a horizontal distance between the X-ray generation unit and X-ray imaging unit.

A sixth aspect of the present invention provides the X-ray radiographic apparatus according to any of the first to fourth aspects, wherein the X-ray control device, upon determination of a field-of-view area by the field-of-view area determination device, adjusts a height position in the vertical direction of the X-ray source to a center position of the field-of-view area, and controls an aperture angle provided by the X-ray movable diaphragm so that the X-ray is applied only to the determined field-of-view area, based on a horizontal distance between the X-ray generation unit and X-ray imaging unit.

In other words, the invention according to the fifth aspect is configured so that long length imaging is performed by means of an X-ray tube turning method, and the invention according to the sixth aspect is configured so that long length imaging is performed by means of an X-ray tube parallel movement method.

An seventh aspect of the present invention provides an X-ray radiographic method for providing a long length of image by adjusting a field of view of an X-ray provided from an X-ray source, taking a plurality of X-ray images of a subject while controlling a position in a vertical direction of an X-ray flat panel detector, and connecting the plurality of images obtained from the X-ray flat panel detector, the method comprising the steps of: providing a screen at a predetermined position ahead of the X-ray flat panel detector, the screen supporting the subject to prevent the subject from moving, the screen being provided with a marker for alignment between a plurality of X-ray images taken during long length imaging; setting in advance an area of the X-ray flat panel detector on which the marker may be projected as a fixed overlapping area, according to a movement range of the X-ray source during long length imaging; setting an imaging area for the long length imaging; determining first to n-th field-of-view areas ($FOV_1$ to $FOV_n$) for dividing the set imaging area into n (n: an integer of no less than 2) areas and taking images, the determining including determining each of the field-of-view areas so that adjacent field-of-view areas overlap each other at the set fixed overlapping area; moving the X-ray flat panel detector to a first position so that an X-ray is applied to the determined first field-of-view area ($FOV_1$); applying an X-ray from the X-ray source only to the first field-of-view area ($FOV_1$) after moving the X-ray flat panel detector to the first position, to make a first exposure; moving the X-ray flat panel detector to a second position after the first exposure so that an X-ray is applied to the determined second field-of-view area ($FOV_2$); and applying an X-ray from the X-ray source only to the second field-of-view area ($FOV_2$) after the X-ray flat panel detector moving to the second position, to make a second exposure, wherein the X-ray flat panel detector is sequentially moved from the first position to a n-th position, and the first to n-th exposures are sequentially made.

According to the present invention, regardless of the conditions for long length imaging (long length imaging area, the X-ray source height and the object distance), long length imaging can automatically be performed so that an alignment marker is unfailingly positioned in an overlapping area of an X-ray flat panel detector, enabling provision of a long length of image in which images are connected with good accuracy using markers shown in the overlapping areas of the respective adjacent images.

DETAILED DESCRIPTION OF THE PREFERRED EMBODIMENTS

Hereinafter, preferred embodiments of an X-ray radiographic apparatus and method according to the present invention will be described with reference to the accompanying drawings.

<Apparatus Configuration>

Figure 1:
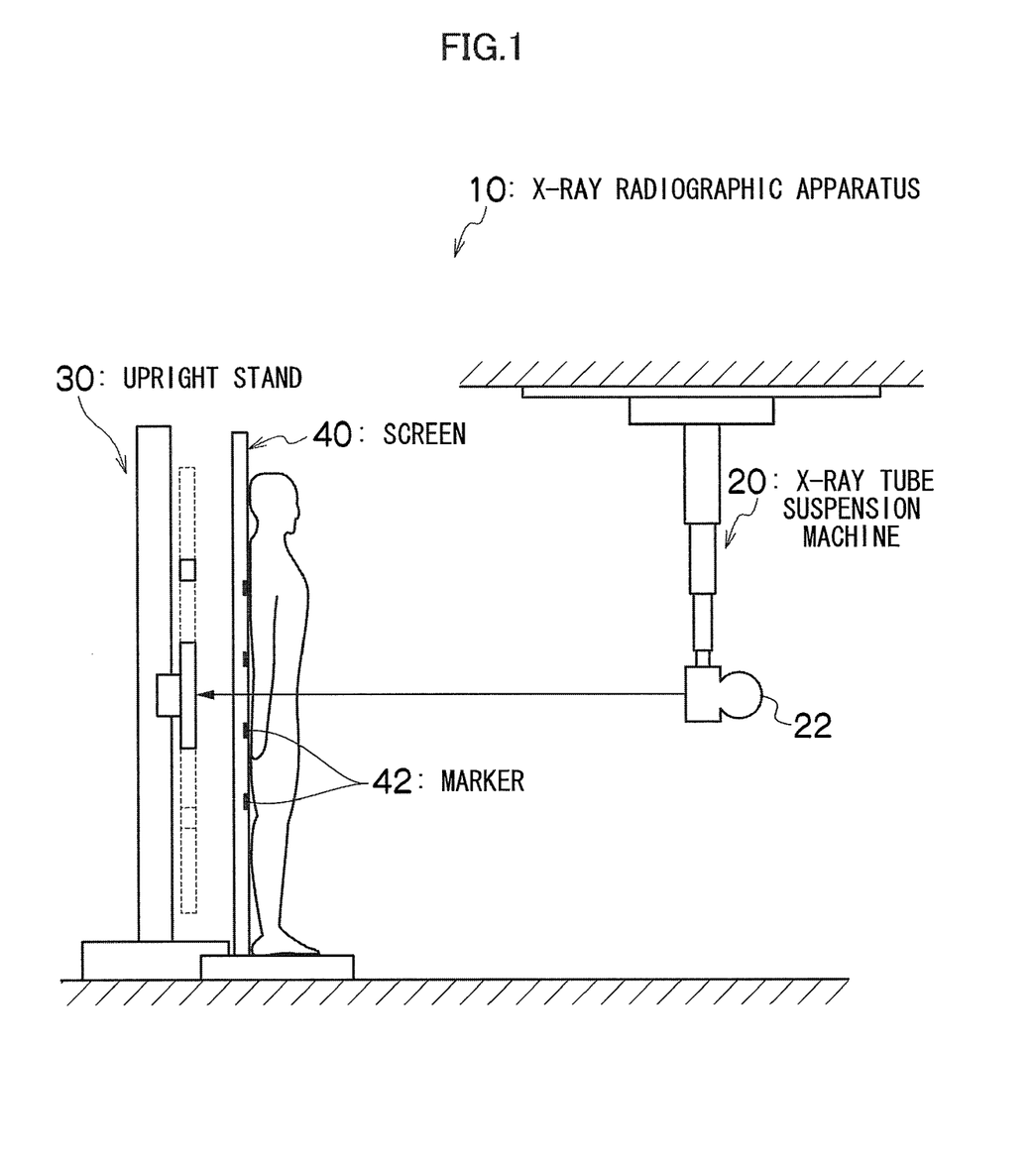
FIG. 1 is a schematic overview of an appearance of an X-ray radiographic apparatus according to the present invention.
Figure 2:
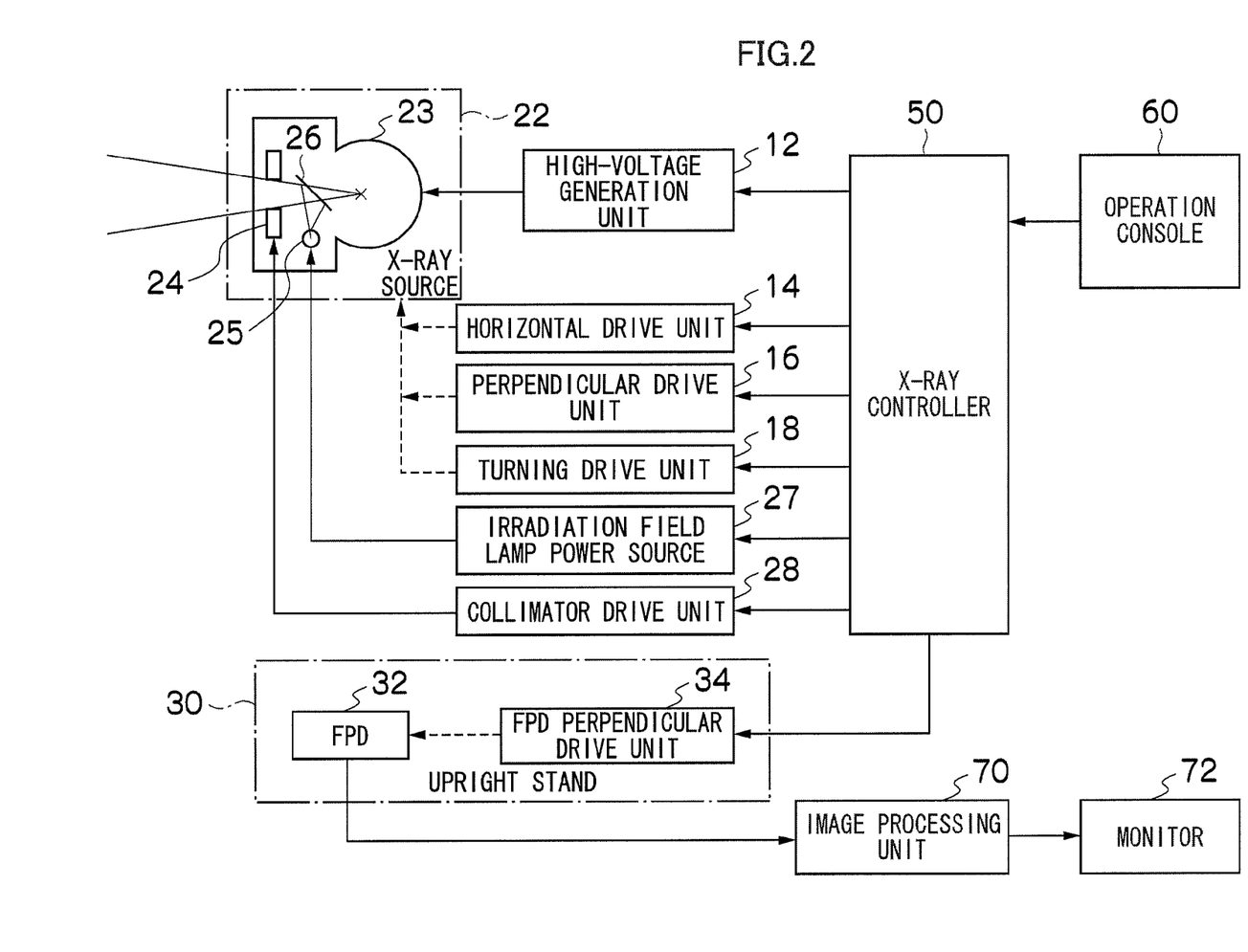
FIG. 2 is a block diagram of an embodiment of an X-ray radiographic apparatus.

FIG. 1 is a schematic overview of the appearance of an X-ray radiographic apparatus according to the present invention, and FIG. 2 is a block diagram of an embodiment of an X-ray radiographic apparatus.

As illustrated in FIGS. 1 and 2, this X-ray radiographic apparatus 10 mainly includes an X-ray tube suspension machine 20, an upright stand 30, a screen 40, an X-ray controller 50, an operation console 60 and an image processing unit 70.

The X-ray tube suspension machine 20 supports an X-ray source 22, and moves this X-ray source 22 in a horizontal direction by means of an overhead travelling-type horizontal drive unit 14, and also moves the X-ray source 22 in a perpendicular (vertical) direction by means of a perpendicular drive unit 16. Also, the X-ray source 22 is configured so that it can be driven to turn by means of a turning drive unit 18, enabling control of the direction of X-ray irradiation.

The X-ray source 22 includes an X-ray tube 23, an X-ray movable diaphragm (collimator) 24, an irradiation field lamp 25, and a mirror 26.

The X-ray tube 23 emits an X-ray by means of a high voltage applied from a high-voltage generation unit 12. The collimator 24 has upper, lower, left and right diaphragm blades that limit an X-ray, and these diaphragm blades are driven by a collimator drive unit 28, thereby the field of view of an X-ray emitted from the X-ray tube 23 being adjusted.

The irradiation field lamp 25 is turned on by power supplied from an irradiation field lamp power source 27, and provides illumination light to a subject via the mirror 26 and the collimator 24. An X-ray's field of view can be identified by means of the illumination light applied to a surface of the subject's body.

The upright stand 30 supports an X-ray flat panel detector (FPD) 32, and moves this FPD 32 in the perpendicular (vertical) direction by means of an FPD perpendicular drive unit 34.

The FPD 32 converts an incoming X-ray into electrical signals, and outputs these electrical signals to the image processing unit 70 as X-ray image signals. The image processing unit 70 performs various image processing, such as offset (dark-current) correction, denoising, gradation conversion, on the input image signals, and also performs, e.g., processing for connecting plural images at the time of long length imaging, and generates X-ray image signals to be displayed on a monitor 72.

The screen 40 is provided at a predetermined position ahead of the upright stand 30 at the time of long length imaging, in order to support a subject to prevent the subject from moving, and markers 42, which are made of, e.g., lead, are embedded in the screen 40 at predetermined intervals in the vertical direction. These markers 42 are embedded in the right and left portions of the screen 40.

The operation console 60 includes, e.g., an X-ray irradiation switch, an imaging condition input unit, and a switch for switching between normal imaging/long length imaging, and an operation instruction input via the operation console 60 is provided to the X-ray controller 50.

The X-ray controller 50 has a microprocessor configuration including a memory unit that stores a central processing unit (CPU), processing programs, various parameters, and the CPU controls the entire apparatus according to signals input from the operation console 60 and the processing programs.

At the time of normal imaging (when making one X-ray image), automatic coordination is performed so that the height of the X-ray source 22 and the height of the FPD 32 correspond to each other, providing efficient and reliable X-ray radiography.

Also, at the time of long length imaging according to the present invention (when taking plural X-ray images while changing the imaging areas), plural images are automatically taken while controlling the position of the FPD 32 and also controlling an X-ray's field-of-view area.

<Long Length Imaging Apparatus Configuration>

Figure 3:
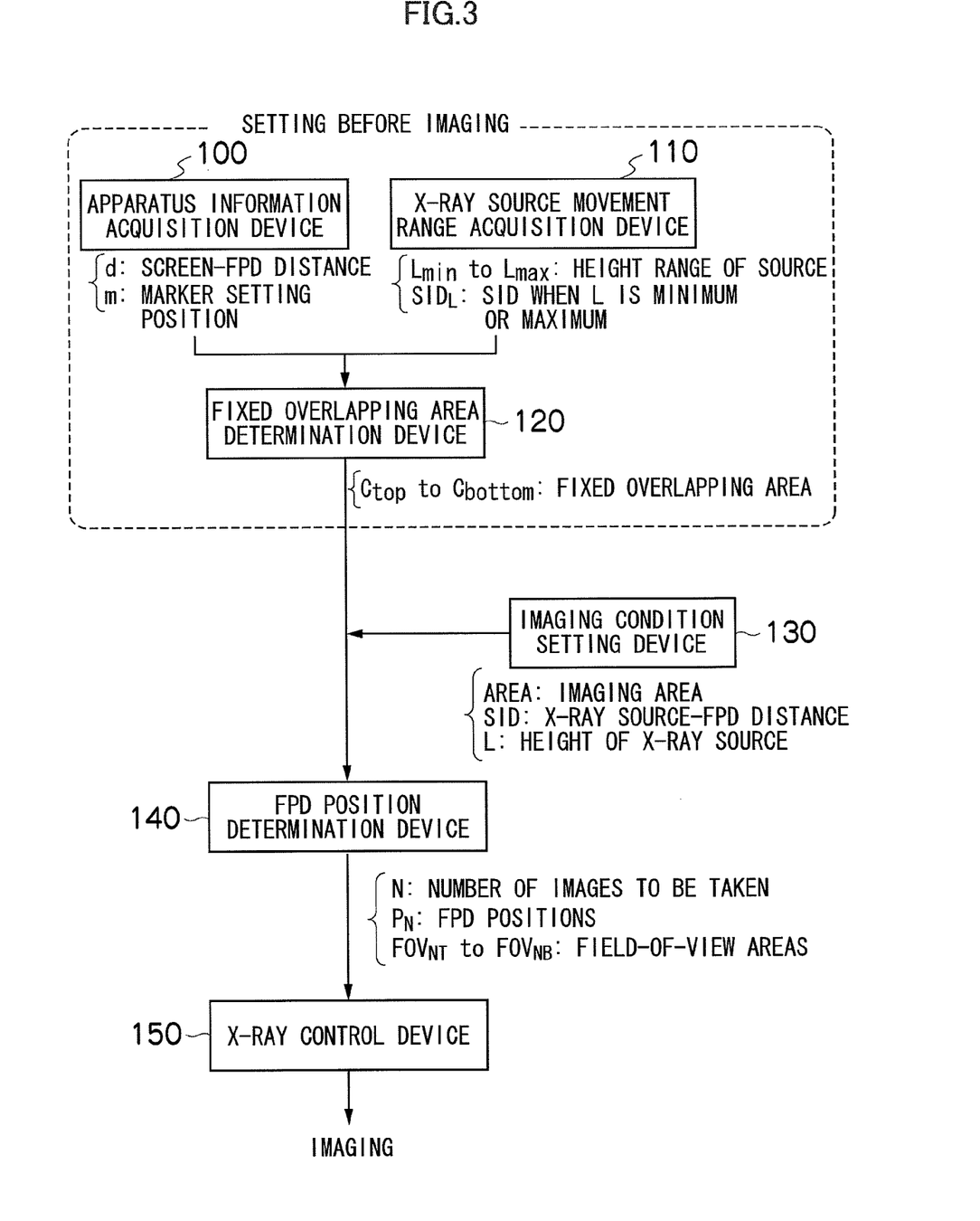
FIG. 3 is a functional block diagram illustrating functions of an X-ray controller and an operation console during long-length imaging.

FIG. 3 is a functional block diagram illustrating functions of the X-ray controller 50 and the operation console 60 during long length imaging.

In FIG. 3, an apparatus information acquisition device 100 and an X-ray source movement range acquisition device 110 acquire various information before imaging, and a fixed overlapping area determination device 120 determines a fixed overlapping area, which will be described later, based on the acquired information.

[Apparatus Information Acquisition Device 100]

Figure 4:
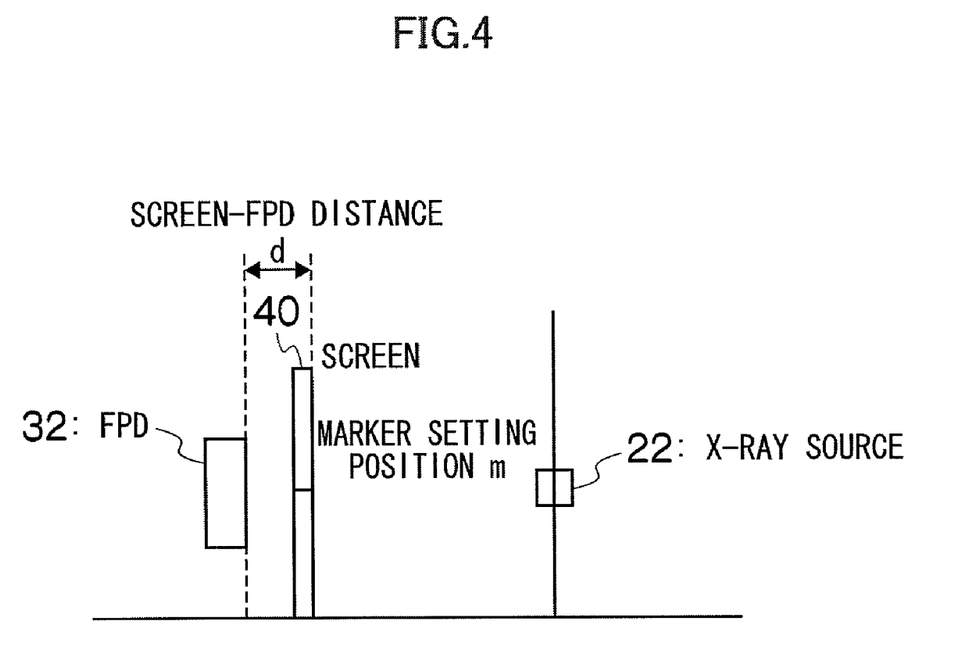
FIG. 4 is a diagram used for describing information determined depending on the installation of an X-ray radiographic apparatus.

The apparatus information acquisition device 100 acquires information determined depending on the installation of the apparatus as illustrated in FIG. 4.

The information acquired by the apparatus information acquisition device 100 includes a screen-FPD distance (d), and a marker setting position (m) indicating the height position of a marker 42.

[X-ray Source Movement Range Acquisition Device 110]

System Movement Range of the X-ray Source

Figure 5:
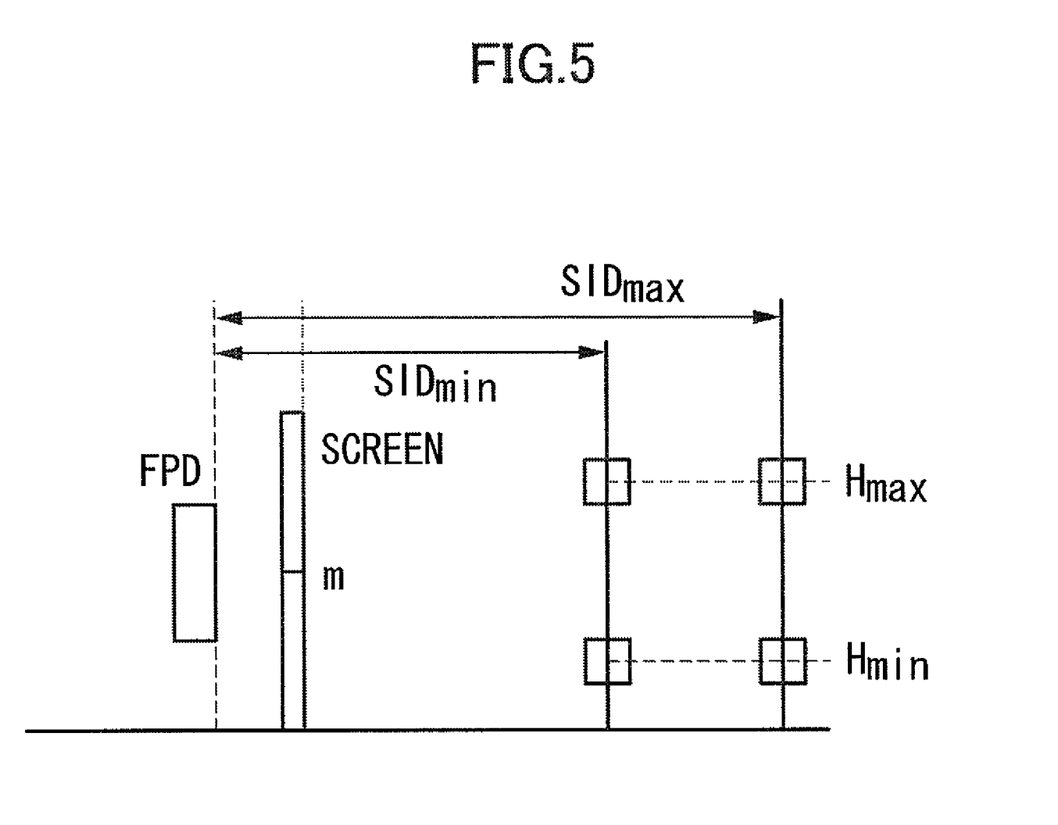
FIG. 5 is a diagram used for describing a system movement range of an X-ray source.

As illustrated in FIG. 5, the minimum and maximum of the X-ray source-FPD distance (SID) when the X-ray source is moved in the horizontal direction are $SID_{min}$ and $SID_{max}$, respectively, and the minimum and maximum of the X-ray source height (H) when the X-ray source is moved in the perpendicular direction are $H_{min}$ and $H_{max}$, respectively. The system movement range of the X-ray source 22 is determined depending on the system specifications.

Range In Which the X-ray Source Can Move During Long Length Imaging

The range in which the X-ray source can actually move during long length imaging within the system movement range is acquired.

Figure 6A:
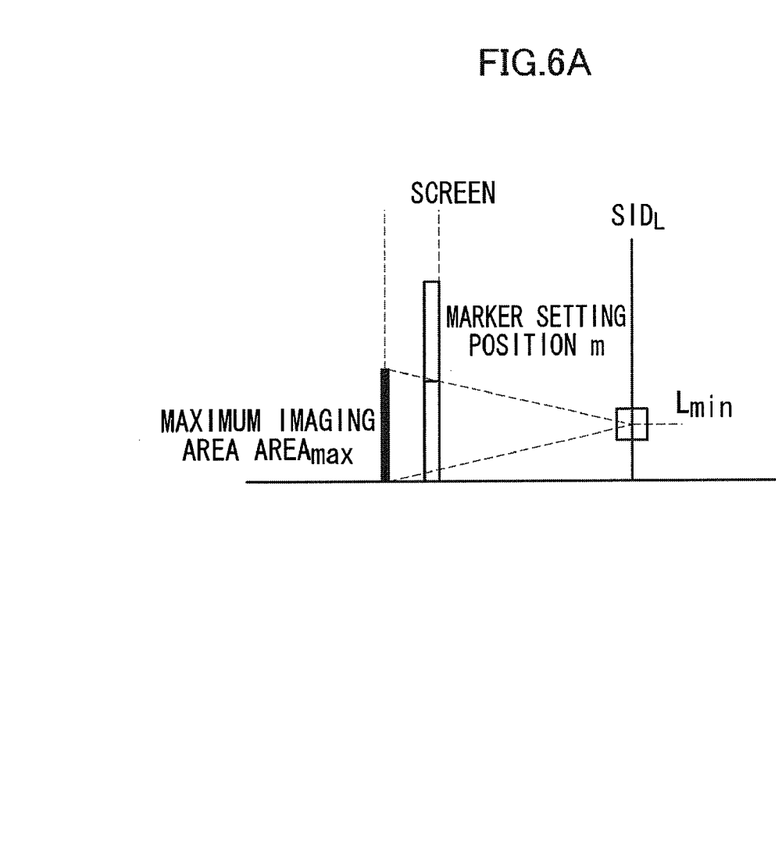
FIGS. 6A and 6B are diagrams used for describing a range in which an X-ray source can move during long-length imaging.
Figure 6B:
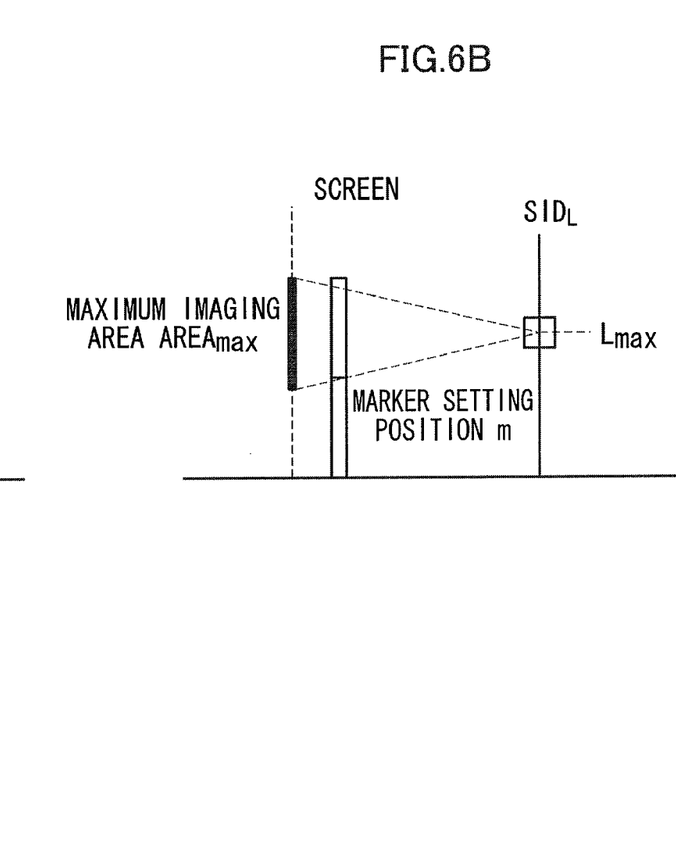

As illustrated in FIGS. 6A and 6B, where the maximum imaging area for long length imaging is $AREA_{max}$, the heights ($L_{min}$ and $L_{max}$) of the X-ray source 22 when an X-ray is applied to the marker position (m) at the most acute angle from the X-ray source 22 are calculated based on the maximum imaging area ($AREA_{max}$) and the marker setting position (m). The height ($L_{min}$) of the X-ray source 22 illustrated in FIG. 6A indicates the height when the incident angle of an X-ray relative to the marker setting position (m) is minimum, and the height ($L_{max}$) of the X-ray source 22 illustrated in FIG. 6B indicates the height when the incident angle of an X-ray relative to the marker setting position (m) is maximum. Also, the X-ray source-FPD distance (SID) at those times is $SID_L$.

The X-ray source movement range acquisition device 110 acquires the height range ($L_{min}$ to $L_{max}$) of the X-ray source 22 and the $SID_L$.

Examples of the method for acquiring the aforementioned respective pieces of information ($L_{min}$, $L_{max}$ and $SID_L$) may include a method in which such information is calculated in advance and stored as preset values, a method in which each piece of information itself is input via, e.g., the operation console 60, and a method in which a maximum imaging area ($AREA_{max}$) is input manually to calculate $L_{min}$ and $L_{max}$.

Where the maximum imaging area ($AREA_{max}$) varies for each X-ray source-FPD distance (SID), the height of the X-ray source when the X-ray is applied to the marker position (m) at the most acute angle considering all possible SIDs is calculated.

[Fixed Overlapping Area Determination Device 120]

Figure 7:
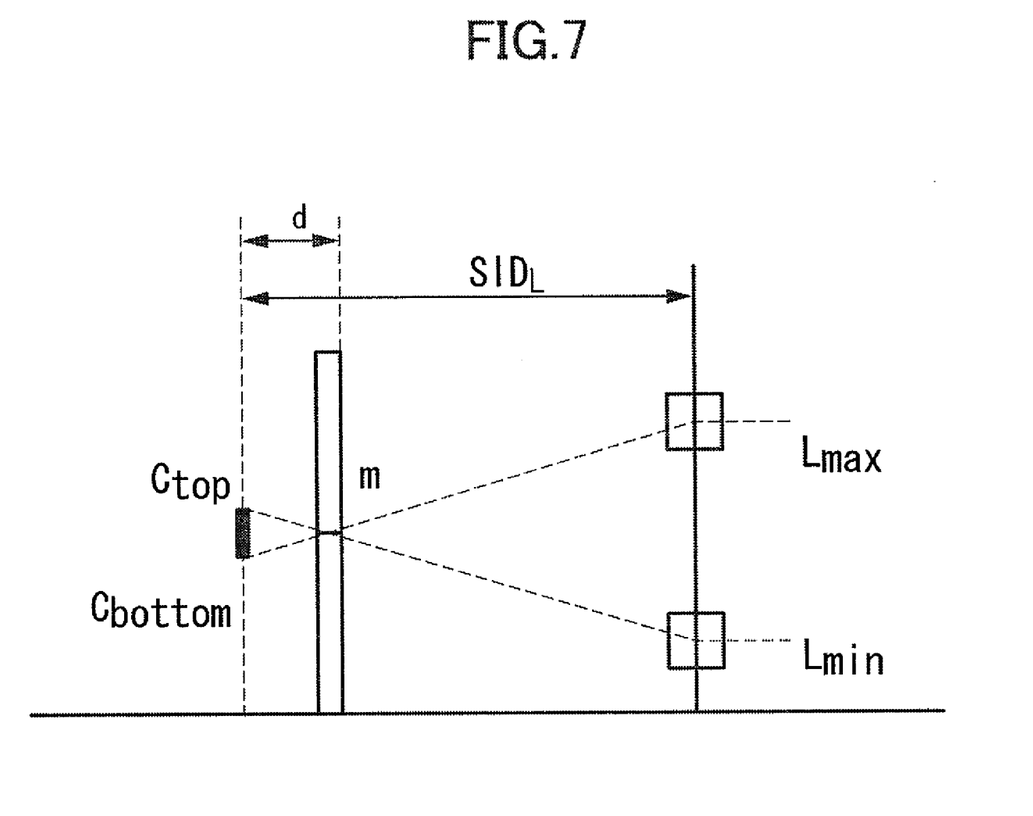
FIG. 7 is a diagram used for describing a fixed overlapping area.

The area of the FPD on which a marker is projected can be calculated from a geometrical relationship as illustrated in FIG. 7, based on the apparatus information (d and m) acquired by the apparatus information acquisition device 100 and the X-ray source movement range information ($L_{min}$, $L_{max}$ and $SID_L$) acquired by the X-ray source movement range acquisition device 110.

In other words, where the position of the top edge of the area of the FPD on which the marker is projected is $C_{top}$ and the position of the bottom edge is $C_{bottom}$, the top edge position ($C_{top}$) and the bottom edge position ($C_{bottom}$) can be expressed by the following equations.

$$C_{top} = L_{min} + (m - L_{min}) \cdot \frac{SID_L}{SID_L - d}$$ [Formula 1]

$$C_{bottom} = \frac{m \cdot SID_L - d \cdot L_{max}}{SID_L - d}$$

The area of $C_{top}$ to $C_{bottom}$ calculated by the equations in [Formula 1] is the area of FPD on which the marker may be projected according to the movement range of the X-ray source 22, and the fixed overlapping area determination device 120 determines this area of $C_{top}$ to $C_{bottom}$ as a fixed overlapping area.

Although in the aforementioned example, the fixed overlapping area ($C_{top}$ to $C_{bottom}$) is determined for one marker position (m), where a plurality of marker positions are provided, the movement range ($Ln_{min}$ to $Ln_{max}$, $SIDn_L$) of the X-ray source is calculated and a fixed overlapping area ($Cn_{top}$ to $Cn_{bottom}$) is determined in a similar manner, for each of the marker positions ($m_n$).

The fixed overlapping areas ($Cn_{top}$ to $Cn_{bottom}$) determined as described above may be stored in the memory device in the X-ray controller 50 as preset values, or may also be calculated based on the apparatus information (d and m) and the X-ray source movement range information ($L_{min}$, $L_{max}$ and $SID_L$).

[Imaging Condition Setting Device 130]

The imaging condition setting device 130 sets a tube voltage, an irradiation dose and a long length imaging area AREA as imaging conditions for long length imaging.

Figure 8:
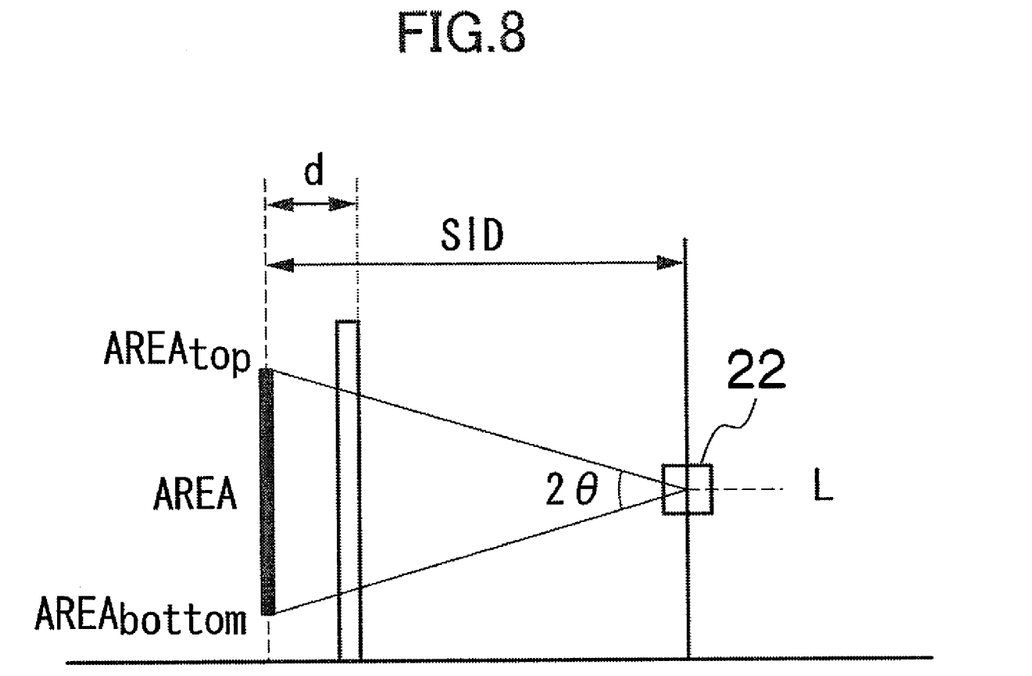
FIG. 8 is a diagram used for describing a method for setting a long length imaging area.

As illustrated in FIG. 8, the long length imaging area (AREA) is set by turning on the irradiation field lamp 25 and adjusting the height (L) of the X-ray source 22 and the aperture angle ($2\theta$) of the collimator 24 to set the area of illumination light applied to a surface of a subject's body. In other words, the top edge position ($AREA_{top}$) and the bottom edge position ($AREA_{bottom}$) of the long length imaging area (AREA) can be calculated by the following equations, based on the adjustment results.

$$AREA_{top} = L + SID \cdot \tan(\theta)$$ [Formula 2]

$$AREA_{bottom} = L - SID \cdot \tan(\theta)$$

The method for setting a long length imaging area (AREA) is not limited to the aforementioned method, and the top edge position ($AREA_{top}$) and the bottom edge position ($AREA_{bottom}$) of a long length imaging area (AREA) may be set manually using the operation console 60.

[FPD Position Determination Device 140]

The FPD position determination device 140 determines the number (N) of images to be taken, field-of-view areas ($FOV_1$ to $FOV_n$) and FPD positions, based on the fixed overlapping area ($C_{top}$ to $C_{bottom}$) determined by the fixed overlapping area determination device 120 and the long length imaging area ($AREA_{top}$ to $AREA_{bottom}$) set by the imaging condition setting device.

Figure 9A:
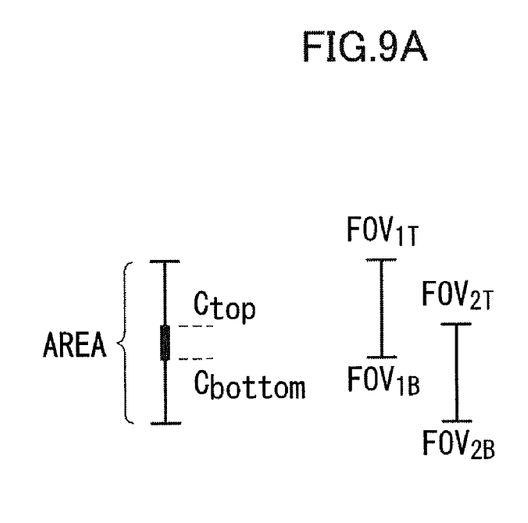
FIGS. 9A and 9B are diagrams used for describing a method for determining field-of-view areas.
Figure 9B:
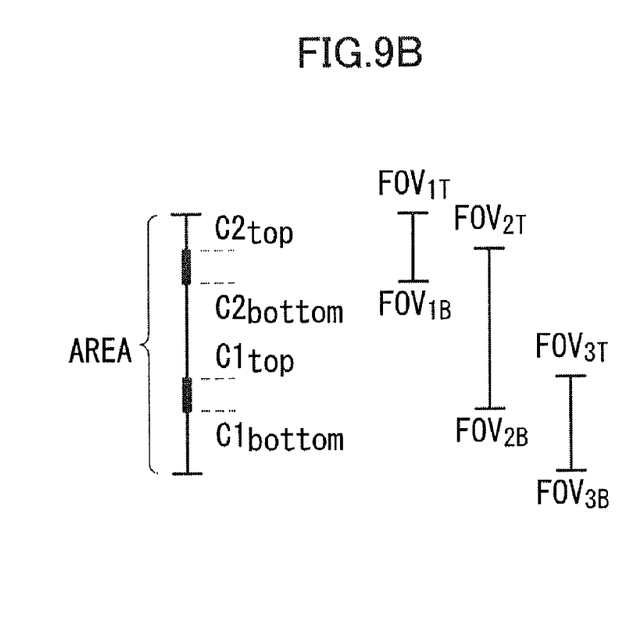

The number (N) of images to be taken is set to be the number of fixed overlapping areas within the long length imaging area ($AREA_{top}$ to $AREA_{bottom}$) plus 1. In other words, as illustrated in FIG. 9A, where the number of fixed overlapping areas within the long length imaging area (AREA) is 1, the number (N) of images to be taken is set to 2, and as illustrated in FIG. 9B, where the number of fixed overlapping areas within the long length imaging area (AREA) is 2, the number (N) of images to be taken is set to 3.

The field-of-view areas ($FOV_1$ to $FOV_n$) corresponding to the number (N) of images to be taken, which have been set as described above, as illustrated in FIGS. 9A and 9B, are determined as the area from the top edge position of the long length imaging area ($AREA_{top}$) to the bottom edge position of the fixed overlapping area ($C_{bottom}$), and the area from the top edge position of the fixed overlapping area ($C_{top}$) to the bottom edge position of the long length imaging area ($AREA_{bottom}$), and, as necessary, areas from the top edge positions of fixed overlapping areas ($C_{top}$) to the bottom edge positions of fixed overlapping areas ($C_{bottom}$).

Figure 10A:
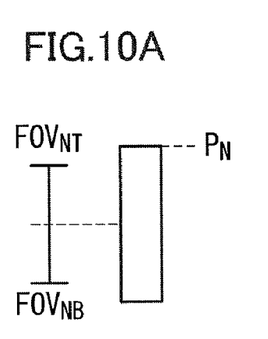
FIGS. 10A, 10B and 10C are diagrams each used for describing a method for determining the position of a FPD.

Meanwhile, the position of the FPD for each of the field-of-view area ($FOV_1$ to $FOV_n$) set as described above, as illustrated in FIGS. 10A, 10B and 10C, is determined on any of a center basis, which is set so that the center position of the field-of-view area and the center position of the FPD correspond to each other (FIG. 10A), a top edge basis, which is set so that the top edge position of the field-of-view area and the top edge position of the FPD correspond to each other (FIG.

Figure 10B:
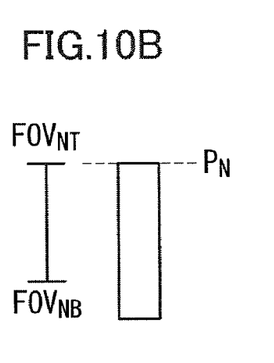
Figure 10C:
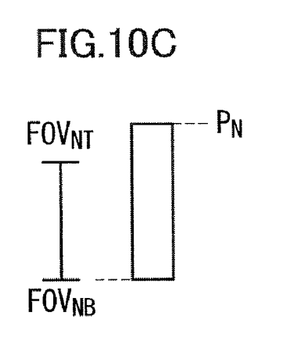

10B) and a bottom edge basis, which is set so that the bottom edge position of the field-of-view area and the bottom edge position of the FPD correspond to each other (FIG. 10C).

[X-ray Control Device 150]

The X-ray control device 150 calculates an X-ray irradiation direction ($\alpha$), a collimator aperture angle ($\theta$) for each field-of-view area, and based on the calculation results, controls the X-ray irradiation direction ($\alpha$) of an X-ray provided from the X-ray source 22 and the collimator aperture angle ($\theta$).

Figure 11A:
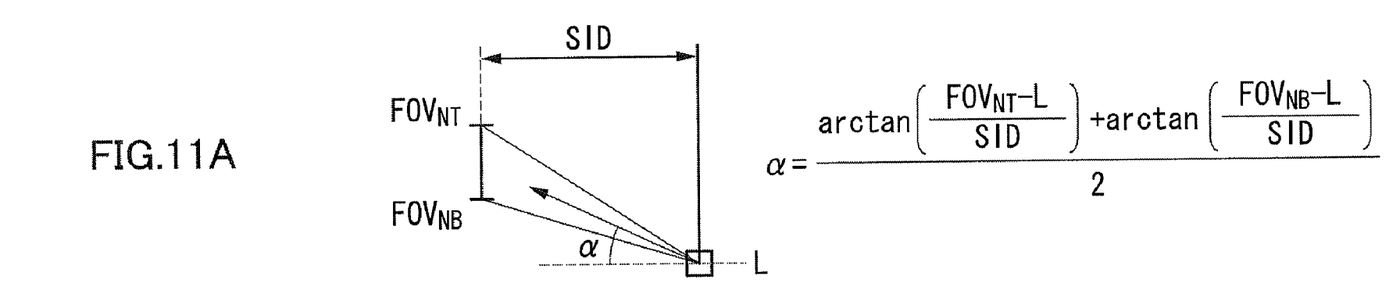
FIGS. 11A and 11B are diagrams used for determining a method for calculating an X-ray irradiation direction ($\alpha$) and a collimator aperture angle ($\theta$)
Figure 11B:
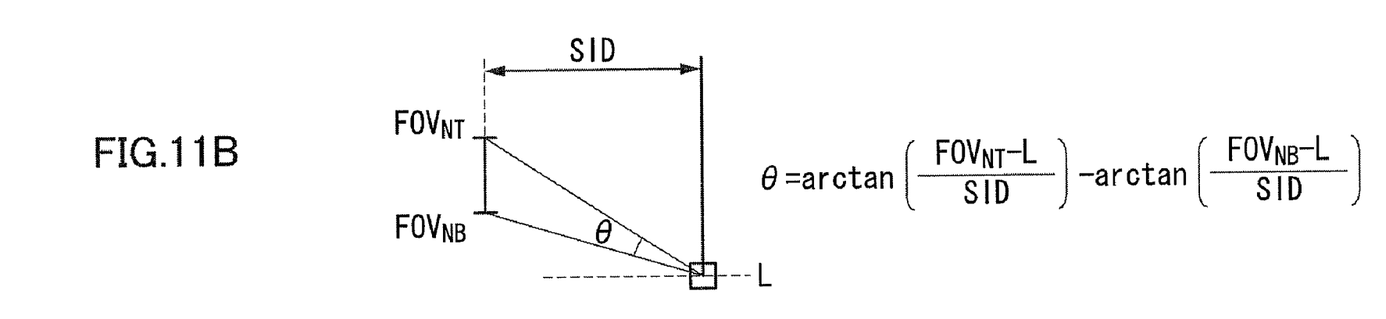

The X-ray irradiation direction ($\alpha$) and the collimator aperture angle ($\theta$) can be calculated by the following equations from a geographic relationship as illustrated in FIGS. 11A and 11B, based on the top edge position ($FOV_{NT}$) and the bottom edge position ($FOV_{NB}$) of a field-of-view area ($FOV_N$), the height (L) of the X-ray source 22, and the X-ray source-FPD distance (SID).

$$\alpha = \frac{\arctan\left(\frac{FOV_{NT} - L}{SID}\right) + \arctan\left(\frac{FOV_{NB} - L}{SID}\right)}{2}$$

$$\theta = \arctan\left(\frac{FOV_{NT} - L}{SID}\right) - \arctan\left(\frac{FOV_{NB} - L}{SID}\right)$$

[Formula 3]

<Operation During Long Length Imaging>

First, the operation console 60 is operated to set the imaging conditions such as the long length imaging area (AREA), the X-ray source-FPD distance (SID), the X-ray source height (L). The fixed overlapping area ($C_{top}$ to $C_{bottom}$) determined for the marker position (m) does not vary for each exposure, and thus, preferably is stored in the memory device in the X-ray controller 50 as a preset value.

The X-ray controller 50, upon the aforementioned imaging conditions being set, as illustrated in FIGS. 9A and 9B, divides the long length imaging area (AREA) into n areas (n=the number of fixed overlapping areas in the long length imaging area plus 1), to determine n field-of-view areas ($FOV_1$ to $FOV_n$), and the position of the FPD 32 corresponding to each field-of-view area.

Subsequently, the X-ray controller 50 moves the FPD 32 to the determined position corresponding to a first field-of-view area ($FOV_1$), and controls the X-ray irradiation direction ($\alpha$) and the collimator aperture angle ($\theta$) so that an X-ray from the X-ray source 22 is applied only to the first field-of-view area ($FOV_1$), and waits ready.

Here, when the X-ray irradiation switch is turned on, an X-ray is applied to the first field-of-view area ($FOV_1$) to make a first X-ray exposure.

Subsequently, upon the end of the first X-ray exposure, the X-ray controller 50 moves the FPD 32 to the determined position corresponding to the second field-of-view area ($FOV_2$), and controls the X-ray irradiation direction ($\alpha$) and the collimator aperture angle ($\theta$) so that an X-ray from the X-ray source 22 is applied only to the second field-of-view area ($FOV_2$) to make a second X-ray exposure.

Upon the end of sequential X-ray exposures according to the number of divisions in the long length imaging areas, the image processing unit 70 performs processing for connecting plural images obtained in the respective X-ray exposures so that the images of markers shown in the fixed overlapping areas of adjacent images are aligned with each other.

Other Embodiments

Although the aforementioned embodiment has been described in terms of an X-ray tube turning method in which plural images are taken while turning an X-ray tube, the present invention is not limited to this method, and can be applied also to an X-ray parallel movement method in which plural images are taken while moving an X-ray tube in parallel to itself.

In this case, upon the determination of a field-of-view area (FOV), the height of the X-ray source is adjusted to the center position of the field-of-view area, and the collimator aperture angle is controlled so that an X-ray is applied only to the field-of-view area.

Also, it should be understood that the present invention is not limited to the above-described examples and that various modifications and variations may be made within the scope not deviating from the spirit of the present invention.

What is claimed is:

1. An X-ray radiographic apparatus comprising:
an X-ray generation unit including an X-ray source, the X-ray source including an X-ray tube and an X-ray movable diaphragm that adjusts a field of view of an X-ray provided from the X-ray tube, and a lifting and lowering device that moves the X-ray source at least in a vertical direction;
an X-ray imaging unit including an X-ray flat panel detector that converts an incoming X-ray into electrical signals, and an upright stand that moves the X-ray flat panel detector in the vertical direction;
a screen provided at a predetermined position ahead of the X-ray imaging unit, the screen supporting a subject to prevent the subject from moving, the screen being provided with a marker for alignment between a plurality of X-ray images taken during long length imaging;
a fixed overlapping area setting device that sets an area of the X-ray flat panel detector on which the marker may be projected as a fixed overlapping area, according to a moveable range of the X-ray source during long length imaging;
an imaging area setting device that sets an imaging area for the long length imaging;
a field-of-view area determination device that determines a plurality of field-of-view areas when dividing the set imaging area into a plurality of areas and taking images, the field-of-view area determination device determining each of the field-of-view areas so that adjacent field-of-view areas overlap each other at the determined fixed overlapping area;
a position determination device that determines a position to which the X-ray flat panel detector is moved for each of the field-of-view areas determined by the field-of-view area determination device so that an X-ray is applied to the field-of-view area;
an upright stand control device that controls the upright stand so that the X-ray flat panel detector is sequentially moved to one of the positions determined by the position determination device for each exposure during the long length imaging; and
an X-ray control device that controls the X-ray generation unit according to one of the field-of-view areas determined by the field-of-view area determination device for each exposure during the long length imaging so that an X-ray is applied only to the field-of-view area.

2. The X-ray radiographic apparatus according to claim 1, wherein the fixed overlapping area is an area from a maximum height position to a minimum height position of the X-ray flat panel detector on which the marker is projected, the area being determined based on horizontal distances among the X-ray generation unit, the screen and the X-ray imaging unit, a position at which the marker is provided, and a minimum incident angle and a maximum incident angle of an X-ray that can be applied to the marker during the long length imaging.

3. The X-ray radiographic apparatus according to claim 1, wherein:
a plurality of the markers are provided in the screen at an interval smaller than a length in the vertical direction of the X-ray flat panel detector; and
the fixed overlapping area setting device sets the fixed overlapping area for each of the markers.

4. The X-ray radiographic apparatus according to claim 2, wherein:
a plurality of the markers are provided in the screen at an interval smaller than a length in the vertical direction of the X-ray flat panel detector; and
the fixed overlapping area setting device sets the fixed overlapping area for each of the markers.

5. The X-ray radiographic apparatus according to claim 1, wherein the position determination device determines the position to which the X-ray flat panel detector is moved so that a center position of one of the field-of-view areas and a center position of the X-ray flat panel detector correspond to each other, a top edge position of one of the field-of-view areas and a top edge position of the X-ray flat panel detector correspond to each other, or a bottom edge position of one of the field-of-view areas and a bottom edge position of the X-ray flat panel detector correspond to each other.

6. The X-ray radiographic apparatus according to claim 4, wherein the position determination device determines the position to which the X-ray flat panel detector is moved so that a center position of one of the field-of-view areas and a center position of the X-ray flat panel detector correspond to each other, a top edge position of one of the field-of-view areas and a top edge position of the X-ray flat panel detector correspond to each other, or a bottom edge position of one of the field-of-view areas and a bottom edge position of the X-ray flat panel detector correspond to each other.

7. The X-ray radiographic apparatus according to claim 1, wherein the X-ray control device, upon determination of a field-of-view area by the field-of-view area determination device, sets a height position in the vertical direction of the X-ray source to be equal to a height position of a center position of the imaging area set by the imaging area setting device, and controls an X-ray irradiation direction of an X-ray from the X-ray source and an aperture angle provided by the X-ray movable diaphragm so that the X-ray is applied only to the determined field-of-view area, based on a horizontal distance between the X-ray generation unit and X-ray imaging unit.

8. The X-ray radiographic apparatus according to claim 6, wherein the X-ray control device, upon determination of a field-of-view area by the field-of-view area determination device, sets a height position in the vertical direction of the X-ray source to be equal to a height position of a center position of the imaging area set by the imaging area setting device, and controls an X-ray irradiation direction of an X-ray from the X-ray source and an aperture angle provided by the X-ray movable diaphragm so that the X-ray is applied only to the determined field-of-view area, based on a horizontal distance between the X-ray generation unit and X-ray imaging unit.

9. The X-ray radiographic apparatus according to claim 1, wherein the X-ray control device, upon determination of a field-of-view area by the field-of-view area determination device, adjusts a height position in the vertical direction of the X-ray source to a center position of the field-of-view area, and controls an aperture angle provided by the X-ray movable diaphragm so that the X-ray is applied only to the determined field-of-view area, based on a horizontal distance between the X-ray generation unit and X-ray imaging unit.

10. The X-ray radiographic apparatus according to claim 8, wherein the X-ray control device, upon determination of a field-of-view area by the field-of-view area determination device, adjusts a height position in the vertical direction of the X-ray source to a center position of the field-of-view area, and controls an aperture angle provided by the X-ray movable diaphragm so that the X-ray is applied only to the determined field-of-view area, based on a horizontal distance between the X-ray generation unit and X-ray imaging unit.

11. An X-ray radiographic method for providing a long length of image by adjusting a field of view of an X-ray provided from an X-ray source, taking a plurality of X-ray images of a subject while controlling a position in a vertical direction of an X-ray flat panel detector, and connecting the plurality of images obtained from the X-ray flat panel detector, the method comprising the steps of:
providing a screen at a predetermined position ahead of the X-ray flat panel detector, the screen supporting the subject to prevent the subject from moving, the screen being provided with a marker for alignment between a plurality of X-ray images taken during long length imaging;
setting in advance an area of the X-ray flat panel detector on which the marker may be projected as a fixed overlapping area, according to a movement range of the X-ray source during long length imaging;
setting an imaging area for the long length imaging;
determining first to n-th field-of-view areas ($FOV_1$ to $FOV_n$) for dividing the set imaging area into n (n: an integer of no less than 2) areas and taking images, the determining including determining each of the field-of-view areas so that adjacent field-of-view areas overlap each other at the set fixed overlapping area;
moving the X-ray flat panel detector to a first position so that an X-ray is applied to the determined first field-of-view area ($FOV_1$);
applying an X-ray from the X-ray source only to the first field-of-view area ($FOV_1$) after moving the X-ray flat panel detector to the first position, to make a first exposure;
moving the X-ray flat panel detector to a second position after the first exposure so that an X-ray is applied to the determined second field-of-view area ($FOV_2$); and
applying an X-ray from the X-ray source only to the second field-of-view area ($FOV_2$) after the X-ray flat panel detector moving to the second position, to make a second exposure, wherein
the X-ray flat panel detector is sequentially moved from the first position to a n-th position, and the first to n-th exposures are sequentially made.

* * * * *